(12) United States Patent
Chen et al.

(10) Patent No.: US 10,620,097 B2
(45) Date of Patent: Apr. 14, 2020

(54) BIOLOGICAL SAMPLE PROCESSING DEVICE

(71) Applicant: Industrial Technology Research Institute, Hsinchu (TW)

(72) Inventors: Chien-An Chen, New Taipei (TW); Wen-Ching Lee, Yunlin County (TW); Tzu-Hui Wu, Tainan (TW); Pei-Shin Jiang, Hsinchu (TW); Ping-Jung Wu, Changhua County (TW); Ruey-Shyan Hong, Taoyuan (TW); Hsiao-Jou Chang, New Taipei (TW); Chun-Chieh Huang, Hsinchu (TW); Ting-Hsuan Chen, Taipei (TW); Chih-Lung Lin, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 463 days.

(21) Appl. No.: 15/381,116

(22) Filed: Dec. 16, 2016

(65) Prior Publication Data

US 2018/0164196 A1    Jun. 14, 2018

(30) Foreign Application Priority Data

Dec. 14, 2016  (TW) .............................. 105141338 A (51) Int. Cl.
    *G01N 1/36*       (2006.01)
    *G01N 1/40*       (2006.01)
    (Continued)

(52) U.S. Cl.
    CPC ................ *G01N 1/36* (2013.01); *B01L 3/508* (2013.01); *B01L 7/52* (2013.01); *C12N 15/10* (2013.01);
    (Continued)

(58) Field of Classification Search
    CPC combination set(s) only.
    See application file for complete search history.

(56) References Cited

U.S. PATENT DOCUMENTS 6,374,684 B1   4/2002 Dority
6,431,476 B1   8/2002 Taylor et al.
(Continued)

FOREIGN PATENT DOCUMENTS

CN    1767897       5/2006
CN    104865393     8/2015
(Continued)

OTHER PUBLICATIONS

Ranjit Prakash et al., "Small volume PCR in PDMS biochips with integrated fluid control and vapour barrier," Sensors and Actuators, Jan. 17, 2006, pp. 398-409.
(Continued)

*Primary Examiner* — Brian R Gordon
(74) *Attorney, Agent, or Firm* — JCIPRNET (57) ABSTRACT

A biological sample processing device includes a base, a purification unit, a metering unit and a first tube. The purification unit is disposed on the base and is configured to purify a sample. The metering unit is disposed on the base and has an inlet, at least one metering trough and an overflow trough. The inlet is connected to the purification unit via the first tube, and the metering trough is connected between the inlet and the overflow trough. The sample from the purification unit is configured to enter the metering unit through the inlet to be moved toward the metering trough, and to be moved toward the overflow trough after the metering trough is filled with the sample.

17 Claims, 11 Drawing Sheets

(51) Int. Cl.
*C12N 15/10* (2006.01)
*B01L 7/00* (2006.01)
*B01L 3/00* (2006.01)
*G01N 33/48* (2006.01)
*C12M 1/42* (2006.01)

(52) U.S. Cl.
CPC . *B01L 2200/025* (2013.01); *B01L 2200/0605* (2013.01); *B01L 2200/0621* (2013.01); *B01L 2200/0631* (2013.01); *B01L 2300/0681* (2013.01); *B01L 2300/0832* (2013.01); *B01L 2300/0867* (2013.01); *B01L 2400/0478* (2013.01); *B01L 2400/0622* (2013.01); *B01L 2400/0644* (2013.01); *C12M 1/42* (2013.01); *G01N 33/48* (2013.01)

(56) References Cited

U.S. PATENT DOCUMENTS

| | | | |
|---|---|---|---|
| 6,440,725 | B1 | 8/2002 | Pourahmadi et al. |
| 6,713,297 | B2 | 3/2004 | McMillan et al. |
| 6,783,934 | B1 | 8/2004 | McMillan et al. |
| 6,818,185 | B1 | 11/2004 | Petersen et al. |
| 6,979,424 | B2 | 12/2005 | Northrup et al. |
| 8,168,442 | B2 | 5/2012 | Petersen et al. |
| 8,394,608 | B2 | 3/2013 | Ririe et al. |
| 8,709,363 | B2 | 4/2014 | Petersen et al. |
| 8,728,765 | B2 | 5/2014 | Ching et al. |
| 8,815,521 | B2 | 8/2014 | Taylor et al. |
| 9,144,419 | B2 | 9/2015 | Poirier et al. |
| 9,212,980 | B2 | 12/2015 | Dority et al. |
| 2001/0012612 | A1 | 8/2001 | Petersen et al. |
| 2006/0177844 | A1 | 8/2006 | Ching et al. |
| 2010/0218621 | A1 | 9/2010 | Chen et al. |
| 2015/0079655 | A1* | 3/2015 | Laugharn, Jr. ......... B01D 43/00 435/173.7 |

FOREIGN PATENT DOCUMENTS

| | | |
|---|---|---|
| TW | 201107038 | 3/2011 |
| TW | M528425 | 9/2016 |
| WO | 0073412 | 12/2000 |
| WO | 0073413 | 12/2000 |
| WO | 2015108082 | 7/2015 |

OTHER PUBLICATIONS

Tsou et al., "DNA methylation analysis: a powerful new tool for lung cancer diagnosis," Oncogene, Sep. 2002, pp. 5450-5461.
Collins et al., "Lung cancer: diagnosis and management," America Family Physician, Jan. 1, 2007, pp. 56-63.
Yanaihara et al., "Unique microRNA molecular profiles in lung cancer diagnosis and prognosis," Cancer Cell, Mar. 2006, pp. 189-198.
Blakemore et al., "Evaluation of the analytical performance of the Xpert MTB/RIF assay." Journal of clinical microbiology, Jul. 2010, pp. 2495-2501.
Marlowe et al., "Evaluation of the Cepheid Xpert MTB/RIF assay for direct detection of Mycobacterium tuberculosis complex in respiratory specimens," Journal of clinical microbiology, Apr. 2011, pp. 1621-1623.
Pilarski et al., "An adaptable microvalving system for on-chip polymerase chain reactions," Journal of Immunological Methods, Oct. 20, 2005, pp. 48-58.
Kim et al., "Fabrication and characterization of a PDMS-glass hybrid continuous-flow PCR chip," Biochemical Engineering Journal, Apr. 2006, pp. 91-97.
Yu et al., "3-D microarrays biochip for DNA amplification in polydimethylsiloxane (PDMS) elastomer," Sensors and Actuators A: Physical, Nov. 2003, pp. 103-107.
Seamer et al., "Sheath fluid control to permit stable flow in rapid mix flow cytometry," Cytometry, Jan. 1999, pp. 75-79.
Thurey et al., "Detail-preserving fluid control," Graphical Models, Jan. 19, 2009, pp. 221-228.
Zheng et al., "Simulation of bubbles," Graphical Models, Aug. 27, 2009, pp. 229-239.
Huang et al., "Near-infrared Raman spectroscopy for optical diagnosis of lung cancer," International Journal of Cancer, Dec. 2003, pp. 1047-1052.
Ramaswamy et al., "Multiclass cancer diagnosis using tumor gene expression signatures," Proceedings of the National Academy of Sciences, Dec. 18, 2001, pp. 15149-15154.
"Office Action of Taiwan Counterpart Application," issued on May 12, 2017, p. 1-p. 3, in which the listed references were cited.

* cited by examiner

BIOLOGICAL SAMPLE PROCESSING DEVICE

CROSS-REFERENCE TO RELATED APPLICATION

This application claims the priority benefit of Taiwan application serial no. 105141338, filed on Dec. 14, 2016. The entirety of the above-mentioned patent application is hereby incorporated by reference herein and made a part of this specification.

TECHNICAL FIELD

The technical field generally relates to a biological sample processing device.

BACKGROUND

In general, a biological sample detection process for disease diagnosis includes the following steps. A biological sample from a patient is firstly collected, and then biological sample is purified by undergoing heating reaction, cleaning, filtering and fluid transferring to remove undesirable element therefrom, so as to separate the target molecule to be detected. Then, the target molecule is driven to perform an amplifying reaction, so the detection device detecting the target molecule is capable of capturing enough signals to perform analysis on whether the patient is ill or not.

The above-mentioned detection process usually requires a large-scale detection apparatus to perform the process, and the technicians need to transfer the biological sample between different machines manually, which leads to problems of cross contamination of the biological sample, infection of biological waste, long operation time and high labor cost.

SUMMARY

Accordingly, one of exemplary embodiments is directed to a biological sample processing device, which is capable of metering a biological sample precisely without having to transfer the biological sample between multiple machines manually during detection.

One of exemplary embodiments provides a biological sample processing device comprises a base, a purification unit, a metering unit and a first tube. The purification unit is disposed on the base and is configured to purify a sample. The metering unit is disposed on the base and has an inlet, at least one metering trough and an overflow trough. The inlet of the metering unit is connected to the purification unit via the first tube, and the metering trough is connected between the inlet and the overflow trough. The sample from the purification unit is configured to enter the metering unit via the inlet to be moved toward the metering trough, and to be moved toward the overflow trough after the metering trough is filled with the sample.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Reference will now be made in detail to the present preferred embodiments of the disclosure, examples of which are illustrated in the accompanying drawings. Wherever possible, the same reference numbers are used in the drawings and the description to refer to the same or like parts.

Figure 1:
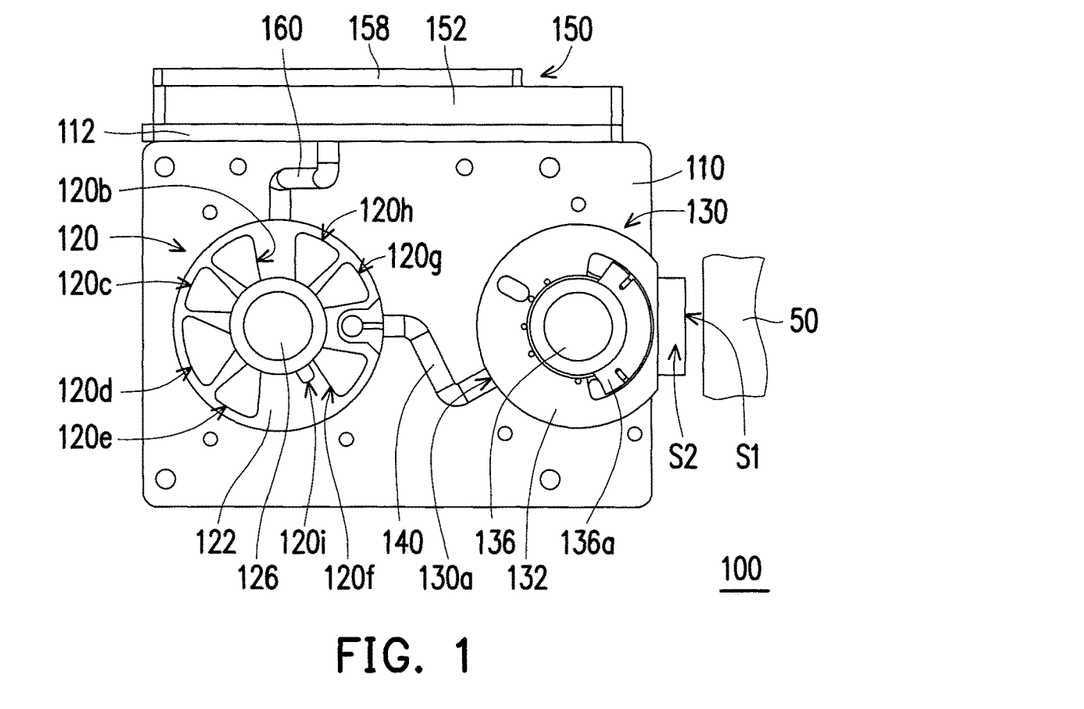
FIG. 1 is a top view illustrating a biological sample processing device according to an exemplary embodiment.
Figure 2:
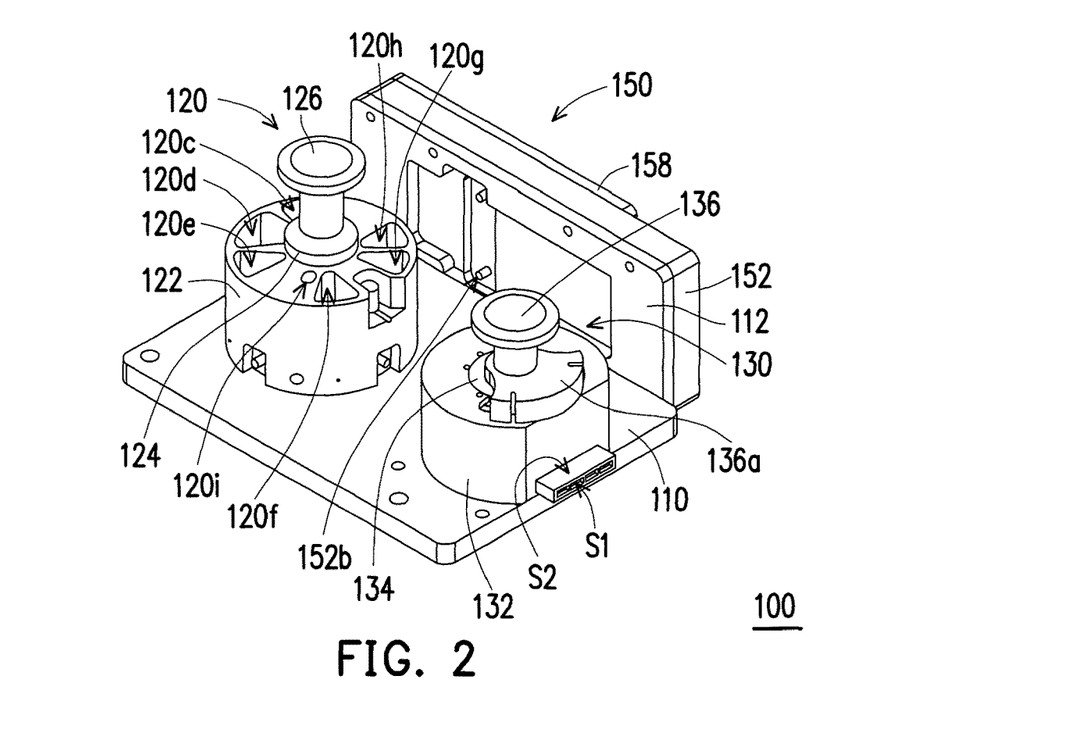
FIG. 2 is a schematic view illustrating a part of the biological sample processing device in FIG. 1.
Figure 3:
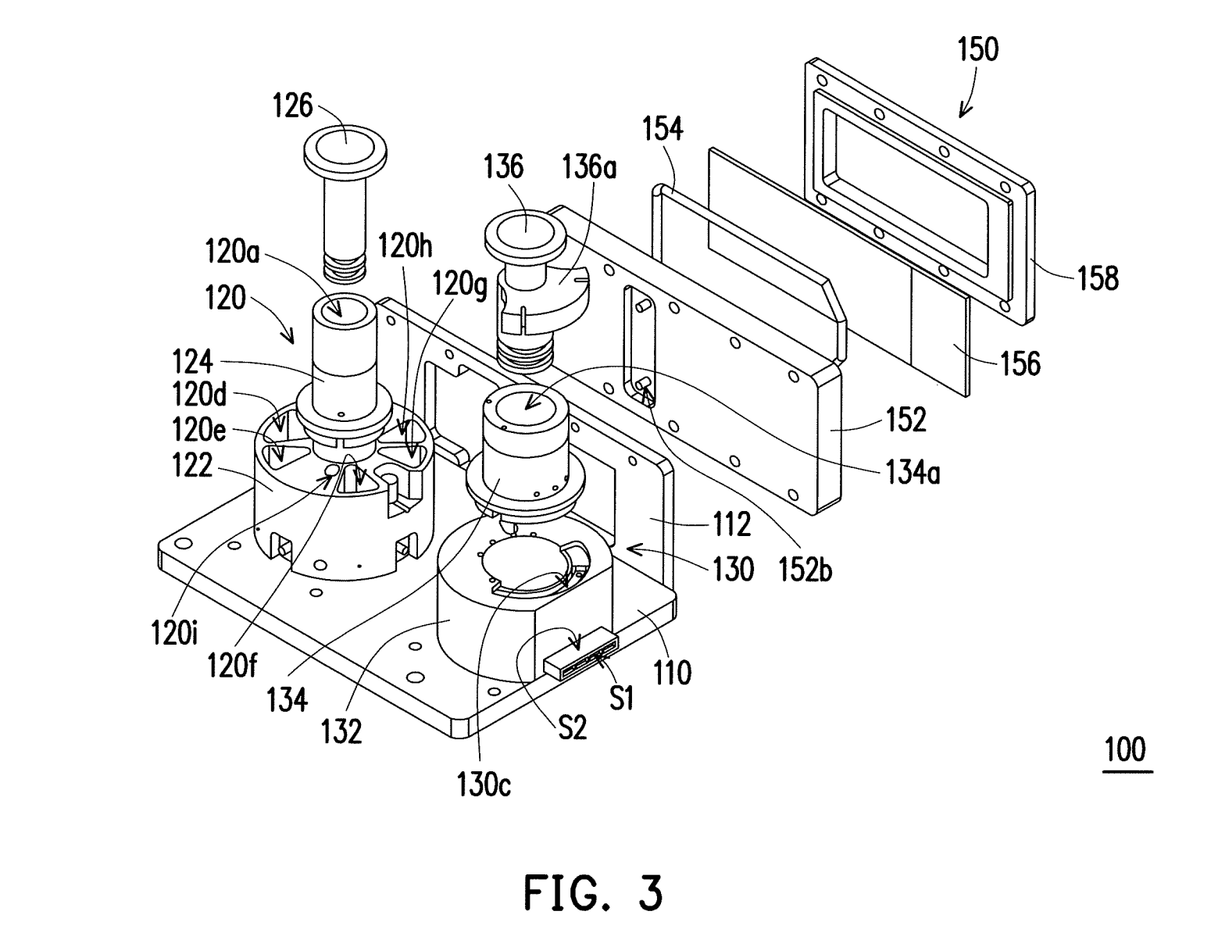
FIG. 3 is an exploded view illustrating the biological sample processing device in FIG. 2.

FIG. 1 is a top view illustrating a biological sample processing device according to an exemplary embodiment. FIG. 2 is a schematic view illustrating a part of the biological sample processing device in FIG. 1. FIG. 3 is an exploded view illustrating the biological sample processing device in FIG. 2. Referring to FIG. 1 to FIG. 3, a biological sample processing device 100 of the present embodiment comprises a base 110, a purification unit 120, a metering unit 130 and a first tube 140. The purification unit 120 is disposed on the base 110 and is configured to purify a sample. The metering unit 130 is disposed on the base 110 and has an inlet 130a. The inlet 130a is connected to the purification unit 120 via the first tube 140. The sample is configured to flow from the purification unit 120 to the metering unit 130 via the first tube 140, so as to be metered in the metering unit 130, and then the sample in the metering unit 130 is detected by a detection device 50 as shown in FIG. 1.

As such, the biological sample processing device 100 of the present embodiment integrates the purification unit 120 and the metering unit 130 onto the same base 110, such that the sample purified in the purification unit 120 may be directly transmitted to the metering unit 130 to be metered, and then the detection operation is performed on the sample in the metering unit 130. Accordingly, there is no need to perform manual transfers of the biological sample between multiple machines as the conventional detection process does, so as to avoid cross contamination of biological sample and infection of biological waste, and save operation time and labor cost for detection. In the present embodiment, the biological sample processing device 100 is, for example, a disposal device adapted for one-time use. However, the disclosure is not limited thereto.

Figure 4:
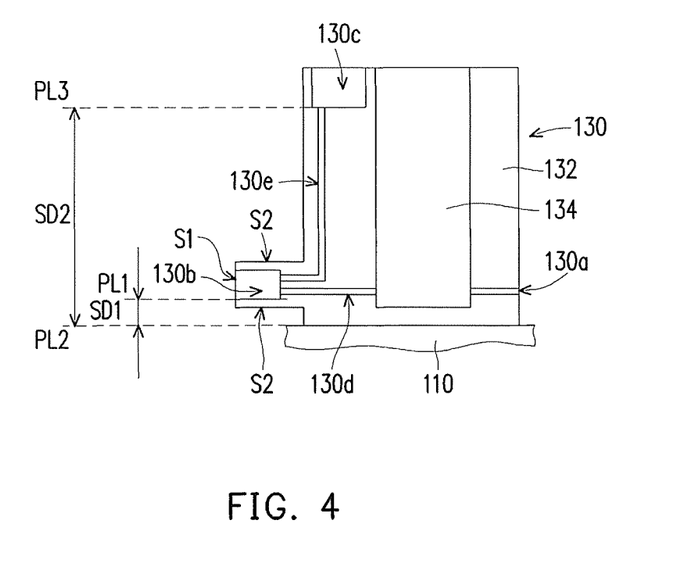
FIG. 4 is a schematic view illustrating a part of the biological sample processing device in FIG. 1.

FIG. 4 is a schematic view illustrating a part of the biological sample processing device in FIG. 1. Referring to FIG. 4, in detail, the metering unit 130 of the present embodiment has at least one metering trough 130b, an overflow trough 130c, at least one first channel 130d and a second channel 130e. The first channel 130d is connected between the inlet 130a and the metering trough 130b. The second channel 130e is connected between the metering trough 130b and the overflow trough 130c. Namely, the metering trough 132 is connected between the inlet 130a and the overflow trough 130c through the first channel 130d and the second channel 130e. The sample from the purification unit 120 is configured to enter the metering unit 130 via the inlet 130a to be moved toward the metering trough 130b via the first channel 130d, and to be moved toward the overflow trough 130c via the second channel 130e after the metering trough 130b is filled with the sample.

Accordingly, in the metering unit 130 of the present embodiment, the metering trough 130b is designed to be connected between the inlet 130a and the overflow trough 130c, such that the sample would indeed fill up the metering trough 130b before flowing to the overflow trough 130c, so as to determine whether the sample is indeed metered in the metering trough 130b or not according to whether the sample appears in the overflow trough 130c or not. In detail, the first channel 130d and the second channel 130e are designed to be connected to the same side of the metering trough 130b as shown in FIG. 3, so that the first channel 130d and the second channel 130e do not face each other, so as to avoid the sample entering the metering trough 130b via the first channel 130d directly flows toward the second channel 130e and reaches the overflow trough 130c without filling up the metering trough 130 first. In another embodiment, a position where the second channel 130e and the metering trough 130b are connected is higher than a position where the first channel 130d and the metering trough 130b are connected, so as to ensure that the metering trough 130b indeed accomplishes metering the sample before the sample enters the second channel 130e.

In the present embodiment, the metering unit 130 has a detection surface. The detection surface may be an end surface S1. The end surface S1 has, for example, diaphaneity and exposes the metering trough 130b, such that the detection device 50 is configured to detect the sample in the metering trough 130b through the end surface S1. In the present embodiment, the detection device 50 is, for example a fluorescent signal detector, configured to detect a fluorescent signal of the sample. In other embodiments, the detection device 50 may be other suitable types of detectors. The disclosure is not limited thereto. In addition, the metering unit 130 of the present embodiment has at least one surface to be heated S2. The surface to be heated S2 is aligned with the metering trough 130b. The heat source is configured to heat the surface to be heated S2, so that the sample in the metering trough 130b undergoes an amplifying reaction, such that the detection device 50 is able to capture enough signals when detecting the sample. The heat source may be a heating device in any suitable form, which is not limited by the disclosure. It is noted that, in the metering unit 130, there is no specific limitation on the detection surface configured to detect the sample. In one embodiment, the surface to be heated S2 may also be the detection surface for detecting the sample.

Referring to FIG. 3 and FIG. 4, in the present embodiment, a first shortest distance SD1 between a first plane PL1 where the metering trough 130b is disposed on and a second plane PL2 where the base 110 is disposed on is shorter than a second shortest distance SD2 between a third plane PL3 where the overflow trough 130c is disposed on and the second plane PL2 where the base 110 is disposed on. Accordingly, the overflow trough 130c is located above the metering trough 130b, so bubbles in the sample in the metering trough 130b may easily float up toward the overflow trough 130c, so as to further enhance the metering accuracy of the metering unit 130. In addition, the design of the position of the overflow trough 130c higher than the position of the metering trough 130b may also ensure the metering trough 130b metering the sample completely before the sample enters the second channel 130e to flow toward the overflow trough 130c. However, the disclosure is not limited thereto. In other embodiments, the relative positions between the metering trough 130b and the overflow trough 130c may be modified according to design requirements.

Figure 5A:
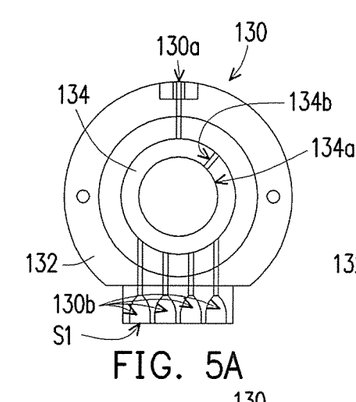
FIG. 5A to FIG. 5F is a schematic view illustrating an operation process of the metering unit in FIG. 1.
Figures 5B, 5C:
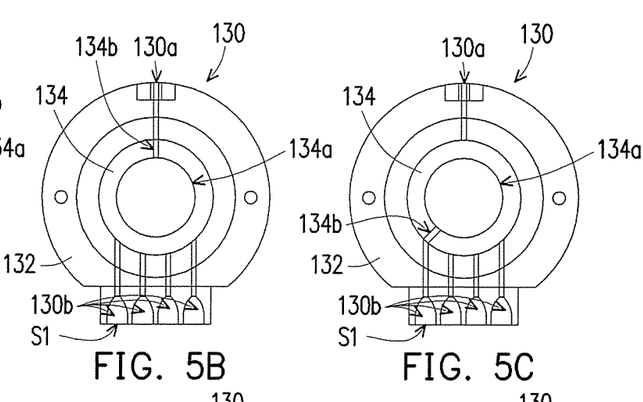
Figure 5D:
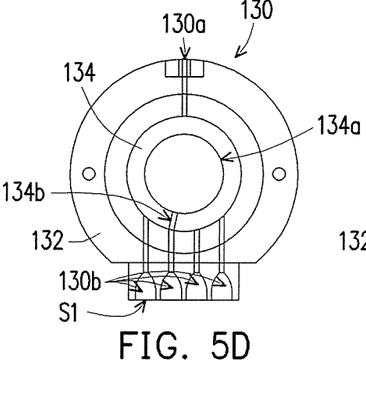
Figures 5E, 5F:
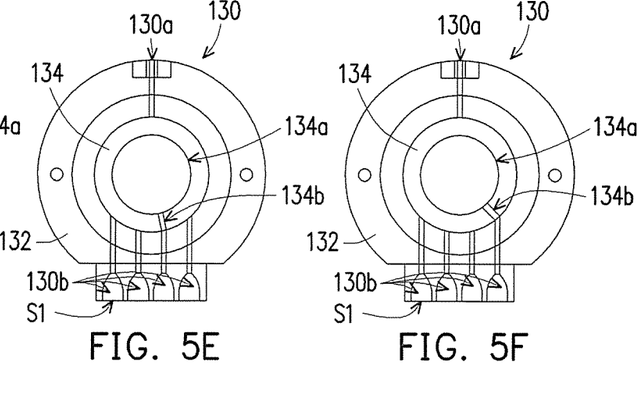

FIG. 5A to FIG. 5F is a schematic view illustrating an operation process of the metering unit in FIG. 1. Referring to FIG. 3 and FIG. 5A, the metering unit 130 of the present embodiment comprises a main body 132 and a rotating component 134. The number of the metering trough 130b is plural (four of the metering troughs 130b are illustrated). The inlet 130a, the metering troughs 130b and the overflow trough 130c are located at the main body 132. The rotating component 134 is disposed between the metering troughs 130b and the inlet 130a. The rotating component 134 has a containing chamber 134a and a guiding channel 134b connected to each other. The rotating component 134 is configured to rotate, such that the guiding channel 134b is aligned with the inlet 130a or any one of the metering troughs 130b. In detail, the rotating component 134 may rotate to the state shown in FIG. 5B, so the guiding channel 134b is aligned with the inlet 130a, such that the sample from the purification unit 120 may enter the containing chamber 134a via the inlet 130a and the guiding channel 134b. Then, the rotating component 134 may rotate to the states shown in FIG. 5C to FIG. 5F in order, so the guiding channel 134b is aligned with the metering troughs 130b in order, such that the sample in the containing chamber 134a may enter the metering troughs 130b via the guiding channel 134b to be metered.

Figure 6:
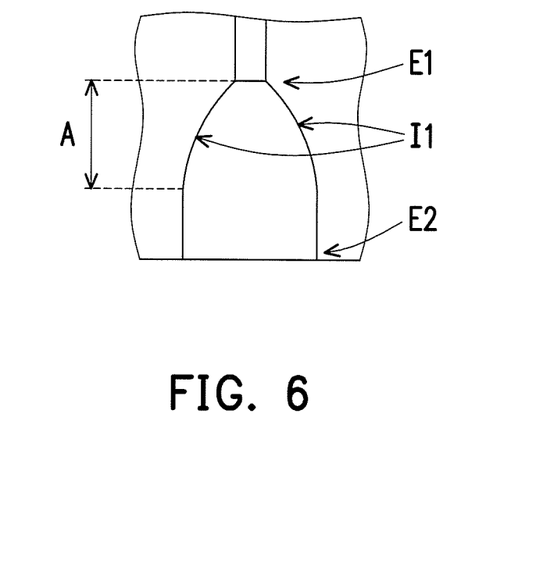
FIG. 6 is an enlarged top view illustrating the metering trough in FIG. 5A.

FIG. 6 is an enlarged top view illustrating the metering trough in FIG. 5A. Referring to FIG. 6, the metering trough 130b of the present embodiment has an opening end E1 and a closing end E2 opposite to each other. The sample is configured to enter the metering trough 130b from the opening end E1. A cross-sectional width of at least a part of the metering trough 130b (illustrated as the section A) increases from the opening end E1 to the closing end E2. Thereby, the metering trough 130b has a guiding slanted surface I1 located therein, such that the sample may flow into the metering trough 130b smoothly by the guidance of the guiding slanted surface I1, so as to avoid occurrence of bubbles in the metering trough 130b due to the sample not flowing smoothly.

Figure 7:
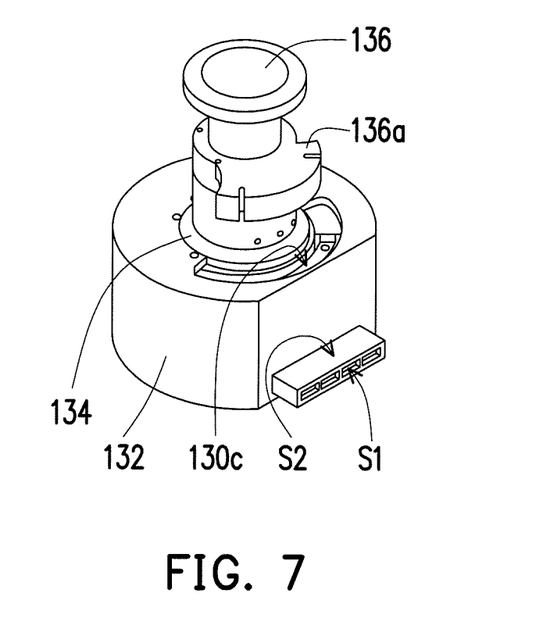
FIG. 7 is a schematic view illustrating the plunger of the metering unit in FIG. 2 moving upward.

FIG. 7 is a schematic view illustrating the plunger of the metering unit in FIG. 2 moving upward. The metering unit 130 of the present embodiment comprises a plunger 136. The plunger 136 is connected to the rotating component 134 and configured to drive the sample in or out of the containing chamber 134a. In detail, the plunger 136 may move from the state shown in FIG. 2 up to the state shown in FIG. 7, so as to drive the sample to move from the purification unit 120 to the containing chamber 134a of the rotating component 134, or the plunger 136 may move from the state shown in FIG. 7 down to the state shown in FIG. 2, so as to drive the sample from the containing chamber 134a of the rotating component 134 moving to the metering trough 130b. To be more specific, the plunger 134 of the present embodiment has a covering portion 136a, and the covering portion 136a is configured to cover the overflow trough 130c along with a downward motion of the plunger 136 for attaining the sealing effect, so as to keep the sample in the metering unit 130 from external contamination.

The means of disposition and function of the purification unit in the present embodiment are described in detail below. Referring to FIG. 1 to FIG. 3, the purification unit 120 has a processing chamber 120a, a sample trough 120b and a plurality of reagent troughs 120c~120i. The processing chamber 120a is connected to the inlet 130a of the metering unit 130 via the first tube 140. The sample trough 120b is configured to contain the sample. The reagent troughs 120c~120i are configured to contain a plurality of reagents required by the detection process. When the sample trough 120b contains the sample, the sample is configured to be moved to the processing chamber 120a from the sample trough 120b. When the reagent troughs 120c~120i contain the reagents, each of the reagents is configured to be moved to the processing chamber 120a from the corresponding reagent trough 120c~120i.

Figure 8A:
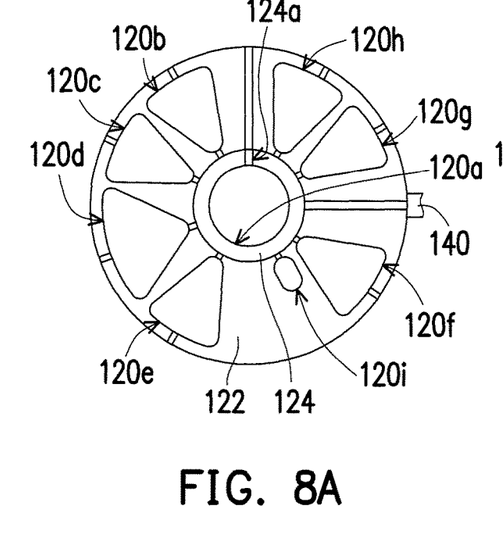
FIG. 8A to FIG. 8J is a schematic view illustrating an operation process of the purification unit in FIG. 1.

FIG. 8A to FIG. 8J is a schematic view illustrating an operation process of the purification unit in FIG. 1. Referring to FIG. 2, FIG. 3 and FIG. 8A, specifically, the purification unit 120 of the present embodiment comprises a main body 122 and a rotating component 124. The sample trough 120b and the reagent troughs 120c~120i are located at the main body 122. The processing chamber 120a is located at the rotating component 124. The rotating component 124 has a guiding channel 124a connected to the processing chamber 120a, and the rotating component 124 is configured to rotate, such that the guiding channel 124a is aligned with the sample trough 120b or any one of the reagent troughs 120c~120i. In detail, the rotating component 124 may rotate to the state shown in FIG. 8B, so the guiding channel 124a is aligned with the sample trough 120b, such that the sample trough 120b is connected to the processing chamber 120a. The rotating component 124 may rotate to the states shown in FIG. 8C to FIG. 8H and FIG. 8J in order, so the guiding channel 124a is aligned with the reagent troughs 120c~120i in order, such that the reagent troughs 120c~120i are connected to the processing chamber 120a, respectively. In addition, the rotating component 124 may rotate to the state shown in FIG. 8I, so the guiding channel 124a is aligned with the first tube 140, such that the sample in the processing chamber 120a may be moved out of the purification unit 120 via the guiding channel 124a and the first tube 140.

Figure 9:
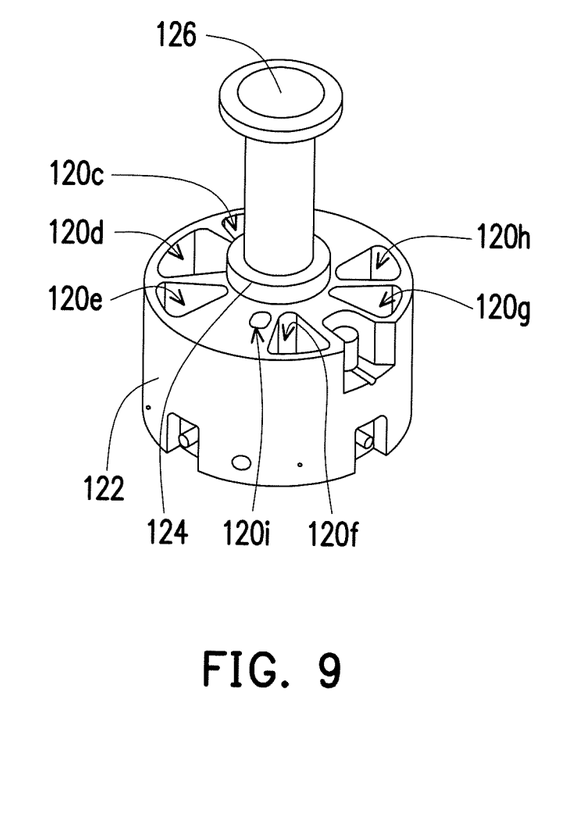
FIG. 9 is a schematic view illustrating the plunger of the purification unit in FIG. 2 moving upward.

FIG. 9 is a schematic view illustrating the plunger of the purification unit in FIG. 2 moving upward. The purification unit 120 of the present embodiment comprises a plunger 126. The plunger 126 is connected to the rotating component 124 and configured to drive the sample and each of the reagents in or out of the processing chamber 120a. In detail, the plunger 126 may move from the state shown in FIG. 2 up to the state shown in FIG. 9 to drive the sample to move from the sample trough 120b into the processing chamber 120a. The plunger 126 may also move from the state shown in FIG. 2 up to the state shown in FIG. 9 to drive the reagents to move from the reagent troughs 120c~120i into the processing chamber 120a, or move from the state shown in FIG. 9 down to the state shown in FIG. 2 to drive the sample to move out of the processing chamber 120a.

Referring to FIG. 1 to FIG. 3, the biological sample processing device 100 of the present embodiment further comprises a section processing unit 150 and a second tube 160. The section processing unit 150 is disposed at a frame 112 located at a side of the base 110, and is connected to the purification unit 120 via the second tube 160. The section processing unit 150 is configured to contain a sample section, and the sample is from the sample section and is moved to the purification unit 120 via the second tube 160.

Figure 10:
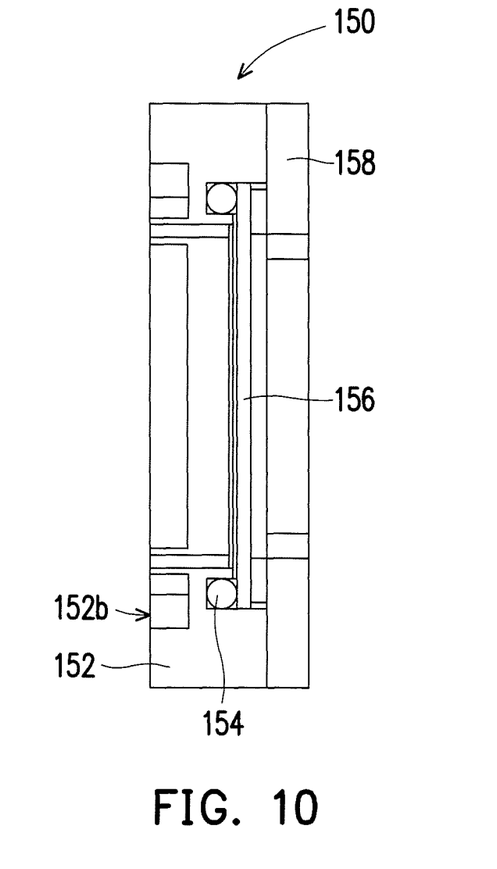
FIG. 10 is a cross-sectional view illustrating the section processing unit in FIG. 1.
Figure 11:
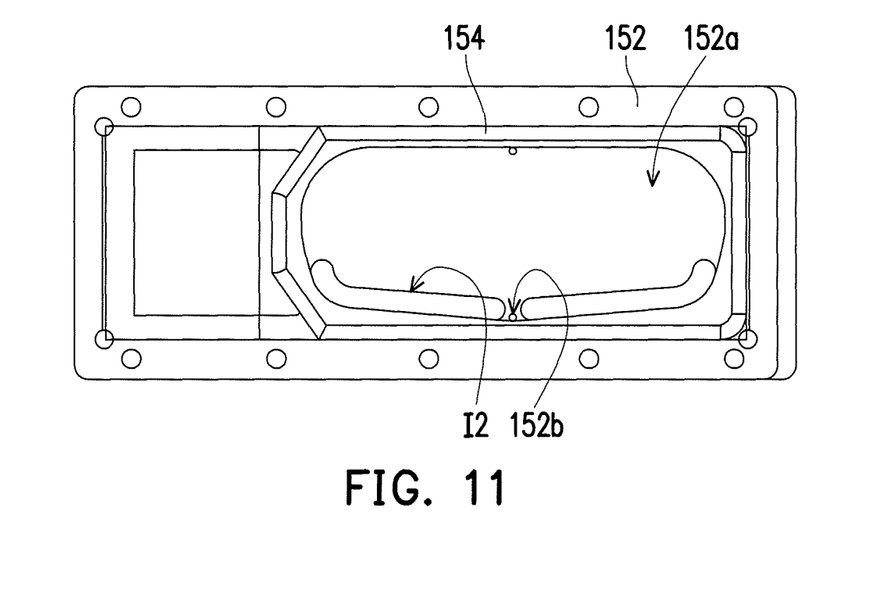
FIG. 11 is a front view illustrating a part of the section processing unit in FIG. 1.

FIG. 10 is a cross-sectional view illustrating the section processing unit in FIG. 1. FIG. 11 is a front view illustrating a part of the section processing unit in FIG. 1. Referring to FIG. 3, FIG. 10 and FIG. 11, specifically, the section processing unit 150 is configured to receive a slide 156, and the section processing unit 150 comprises a main body 152, a sealing component 154 and a cover 158. The slide 156 is configured to carry the sample section and adapted to be disposed between the main body 152 and the cover 158, such that the sample section is located between the main body 152 and the slide 156. The sealing component 154 may be an O-ring and seals between the slide 156 and the main body 156. Referring to FIG. 11, the section processing unit 150 has a containing space 152a and a gateway 152b located at the main body 152. The containing space 152a is configured to contain the sample section and connected to second tube 160 via the gateway 152b, so as to be connected to the purification unit 120 via the second tube 160. To be more specific, the containing space 152a has at least one guiding slanted surface 12, and the guiding slanted surface 12 is configured to guide the sample flow toward the gateway 152b, so as to avoid excessive sample remaining in the containing space 152a. In addition, in one embodiment, under the circumstance of the sample section being a paraffin embedded sample, the cover 158 of the section processing unit 150 may be functioning as a heating assembly. The heating assembly is configured to increase the temperature by adopting suitable heat source, so as to heat the sample section to perform a deparaffinization to the sample section.

Figure 12:
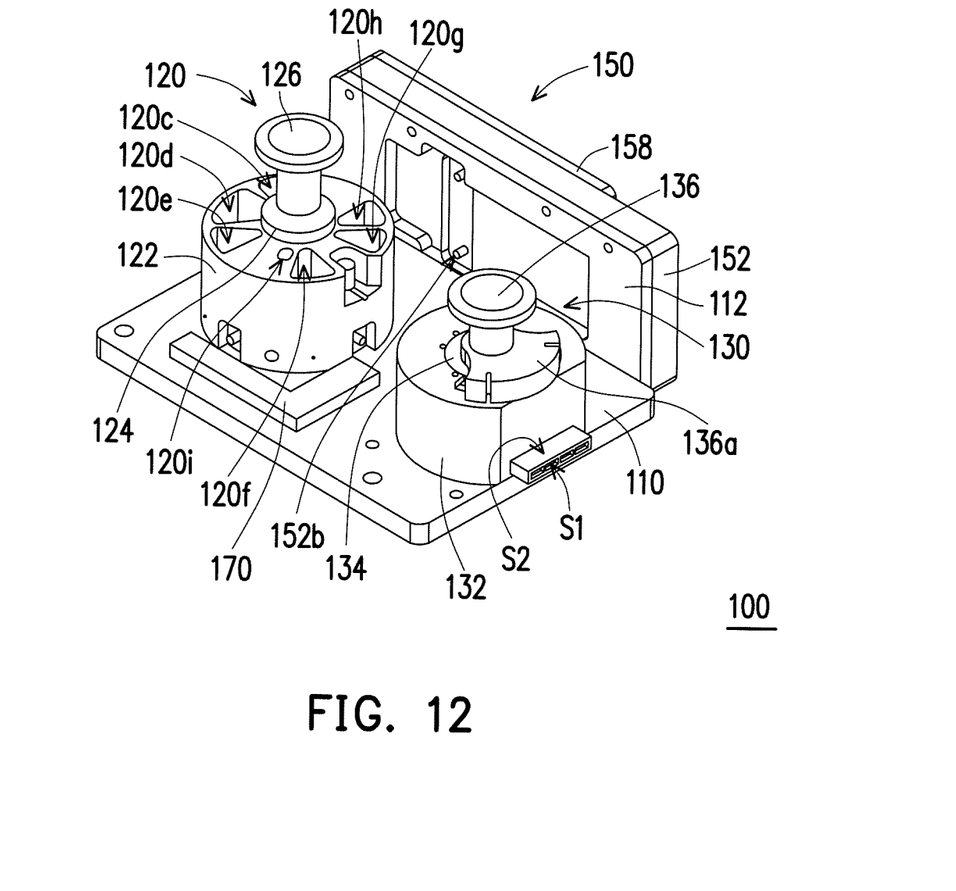
FIG. 12 is a top view illustrating a biological sample processing device according to another exemplary embodiment.

FIG. 12 is a top view illustrating a biological sample processing device according to another exemplary embodiment, which illustrates the biological sample processing device in FIG. 1 additionally equipped with a waste liquid trough. Referring to FIG. 12, the biological sample processing device 100 may further comprise a waste liquid trough 170. The waste liquid trough 170 is disposed at the base 110 and connected to the purification unit 120. The waste liquid generated by the purification unit 120 during purifying process may be discharged to the waste liquid trough 170. The waste liquid trough 170 may be connected to the purification unit 120 via suitable tube or structure, which is not limited by the disclosure. For example, when the waste liquid in the purification unit 120 is discharged to the waste liquid trough 170, the first tube 140 may be temporarily switched to be connected between the purification unit 120 and the waste liquid trough 170, or be temporarily detached, so another tube is connected between the purification unit 120 and the waste liquid trough 170.

The operation method of the biological sample processing device 100 in the present embodiment is described as follows. First of all, the biopsy is disposed at the section processing unit 150, and the deparaffinization is performed to the sample section. The deparaffinization may be omitted if the sample section is not a paraffin embedded sample. Then, the sample is moved to the purification unit 120, and the sample is thoroughly blended with lysis buffer in the purification unit 120, so as to release nucleic acid by breaking cells, bacteria or viruses. The lysis buffer may or may not include proteinase K. A capture buffer is added to the sample in the purification unit 120, so as to lower solubility of the nucleic acid, such that the nucleic acid of the sample is attached to a solid carrier such as a bead, a fibre, a membrane, a filter paper, a macromolecule, or a gel, etc. The waste liquid not containing the nucleic acid of the sample is discharged from the purification unit 120. A wash buffer is added to the sample in the purification unit 120 to wash off non-specific absorption of non-nucleic acid on the solid carrier. The waste liquid of the wash buffer is discharged to the waste liquid trough 170 from the purification unit 120. The solid carrier carrying the nucleic acid of the sample is washed by an amplification buffer in the purification unit 120, such that the nucleic acid is dissolved in the amplification buffer. An amplification enzyme is added to the amplification buffer containing the nucleic acid in the purification unit 120 to perform amplification of the nucleic acid. The amplification buffer containing the amplification enzyme and the nucleic acid is transferred to the metering unit 130 and detected whether it has an amplification signal of the target gene or not by the detection device 50.

Figure 8B:
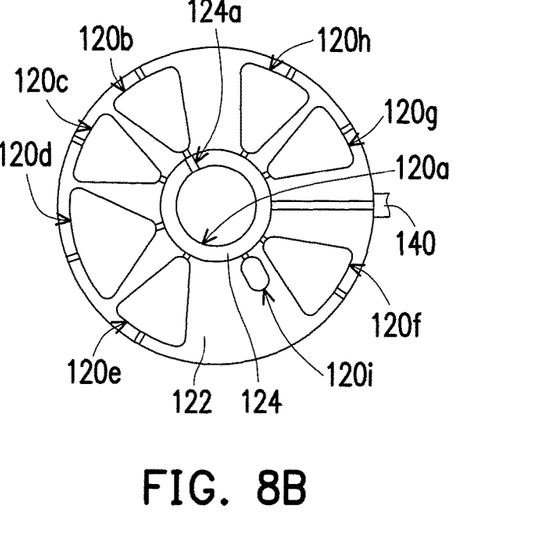
Figure 8C:
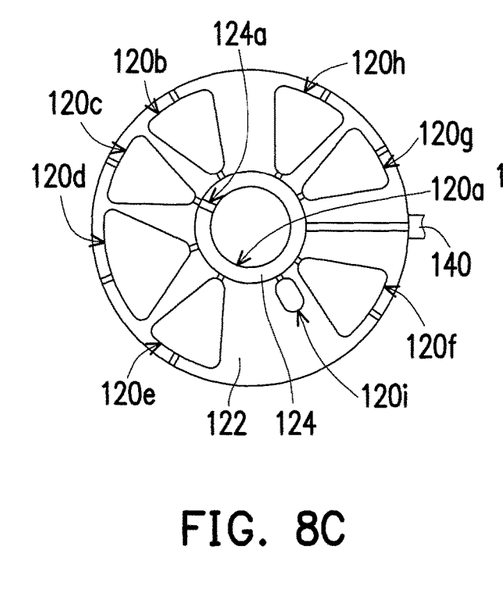
Figure 8D:
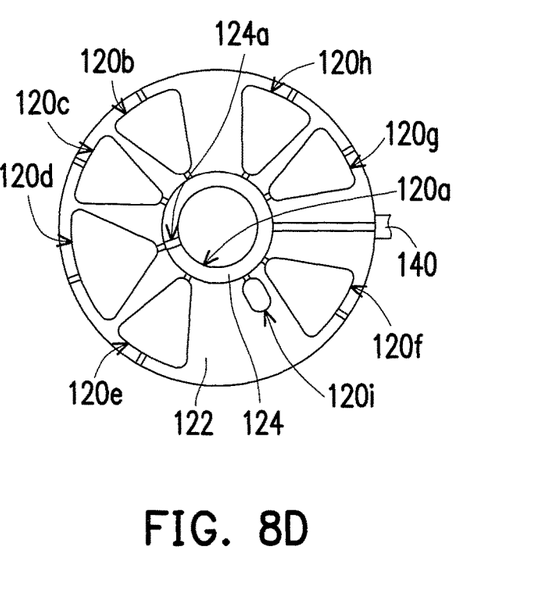

Taking isothermal amplification of liquid biological sample for example to specifically describe the operation process of the purification unit 120 in the biological sample processing device 100 of the present embodiment. First of all, the lysis buffer, the capture buffer, the wash buffer, the amplification enzyme and the amplification buffer are respectively sealed in the reagent troughs 120c~120g of the purification unit 120 in advance, and then a liquid biopsy is injected into the sample trough 120b manually. Then, the rotating component 124 is rotated so that the guiding channel 124a is aligned with the sample trough 120b as shown in FIG. 8B, and the liquid biopsy in the sample trough 120b is drawn to the processing chamber 120a by the plunger 126. The rotating component 124 is rotated so that the guiding channel 124a is aligned with the reagent trough 120c as shown in FIG. 8C, and drawing in and pushing out actions are performed by the plunger 126, such that the liquid biopsy is thoroughly blended with the lysis buffer in the reagent trough 120c. The rotating component 124 is rotated so that the guiding channel 124a is aligned with the reagent trough 120d as shown in FIG. 8D; the capture buffer, e.g. beads, in the reagent trough 120d is drawn to the processing chamber 120a by the plunger 126, and the liquid blending is accomplished by utilizing the plunger 126 to perform the actions of drawing in and pushing out. The blended liquid in the processing chamber 120a is heated to separate out the target molecule, e.g. nucleic acid. Herein, for example, the biological sample processing device 100 may be disposed over a suitable heat source, so as to perform the heating process by the heat source.

Figure 8E:
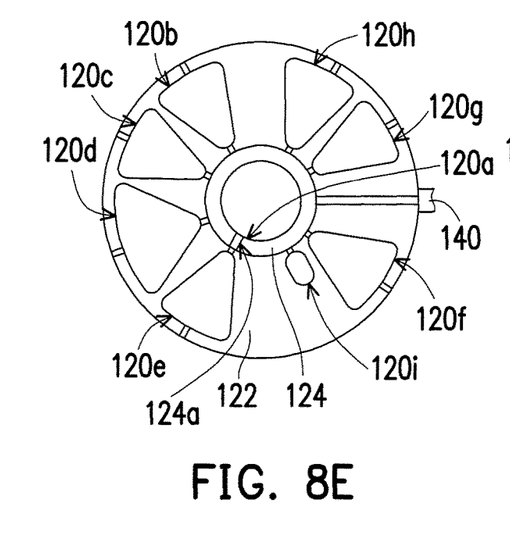
Figure 8F:
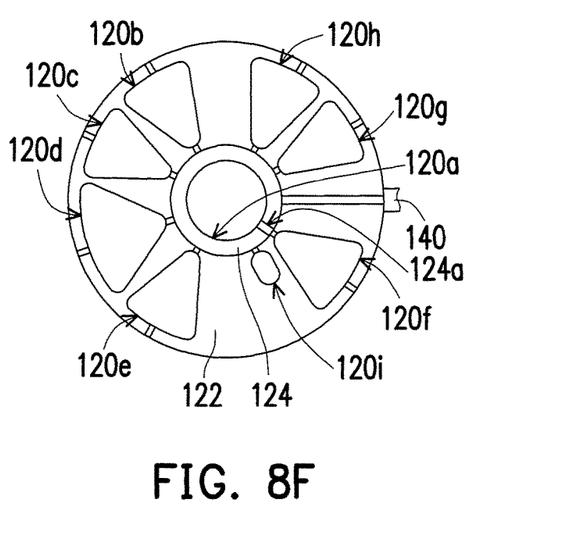
Figure 8G:
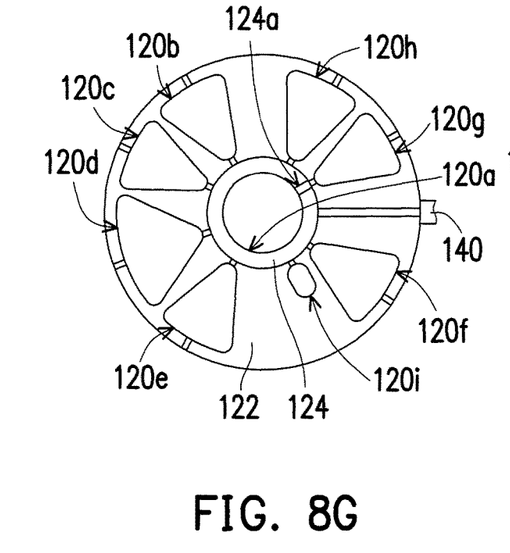
Figure 8H:
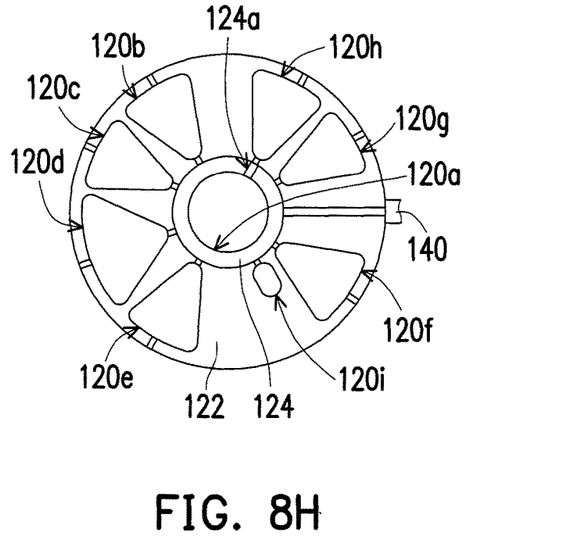
Figure 8I:
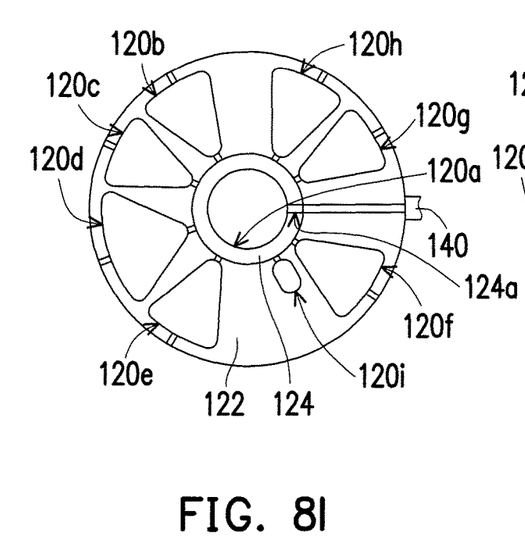

Then, an external magnet is moved underneath the processing chamber 120a. A few minutes later, the waste liquid with non-target molecule impurities is discharged from the processing chamber 120a to the waste liquid trough 170 by plunger 126. At the time, the target molecule is in the processing chamber 120a. The rotating component 124 is rotated so that the guiding channel 124a is aligned with the reagent trough 120e as shown in FIG. 8E, and the wash buffer in the reagent trough 120e is drawn to the processing chamber 120a by the plunger 126. The waste liquid with non-target molecule impurities is discharged from the processing chamber 120a to the waste liquid trough 170 by plunger 126. At the time, the target molecule remains in the processing chamber 120a. The rotating component 124 is rotated so that the guiding channel 124a is aligned with the reagent trough 120f and the reagent trough 120g in order as shown in FIG. 8F and FIG. 8G. The amplification buffer in the reagent trough 120f and the amplification enzyme in the reagent trough 120g are drawn to the processing chamber 120a by the plunger 126, and are thoroughly blended by the plunger 126. The rotating component 124 is rotated so that the guiding channel 124a is aligned with the first tube 140 as shown in FIG. 8I, such that the blended liquid is moved to the metering unit 130 via the first tube 140, and the detection device 50 performs a fluorescent signal detection to the blended liquid after the blended liquid is metered in the metering unit 130.

Taking a thermal cycling amplification of a biological tissue specimen for another example to specifically describe another operation process of the purification unit 120 in the biological sample processing device 100 of the present embodiment. First of all, deparaffin solution, alcohol, capture buffer, wash buffer, lysis buffer, amplification buffer, another wash buffer and proteinase K are respectively sealed in the sample trough 120b and the reagent troughs 120c~120i of the purification unit 120 in advance. A glass fibre membrane is disposed at the intersection of the purification unit 120 and the first tube 140. An amplification enzyme is sealed in the metering trough 130b of the metering unit 130 in advance, and then a paraffin-embedded tissue sample (FFPE) is disposed in the section processing unit 150 manually. Then, the rotating component 124 is rotated so that the guiding channel 124a is aligned with the sample trough 120b as shown in FIG. 8B, and the deparaffin solution in the sample trough 120b is drawn to the processing chamber 120a by the plunger 126. The rotating component 124 is rotated so that the guiding channel 124a is aligned with the section processing unit 150 (illustrated in FIG. 1) as shown in FIG. 8A, and the deparaffin solution in the processing chamber 120a is driven to move to the section processing unit 150 by the plunger 126. The FFPE tissue and the deparaffin solution is heated by the cover 158 to dissolve the paraffin. A waste liquid with dissolved paraffin is moved back to the sample trough 120b by the plunger 126. It is noted that, in the operation process, the sample trough 120b is not configured to contain the sample, but to contain the deparaffin solution and the waste liquid with dissolved paraffin.

Figure 8J:
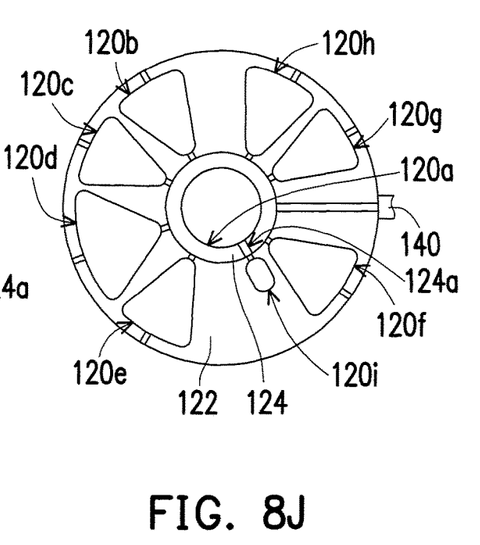

Then, the rotating component 124 is rotated so that the guiding channel 124a is aligned with the reagent trough 120c as shown in FIG. 8C, and the alcohol in the reagent trough 120c is drawn to the processing chamber 120a by the plunger 126. The rotating component 124 is rotated so that the guiding channel 124a is aligned with the section processing unit 150 (illustrated in FIG. 1) as shown in FIG. 8A, and the alcohol in the processing chamber 120a is driven to move to the section processing unit 150 by the plunger 126. After the alcohol is blended with the sample in the section processing unit 150, the waste liquid is moved back to the reagent trough 120c. The rotating component 124 is rotated so that the guiding channel 124a is aligned with the reagent trough 120f and the reagent trough 120i as shown in FIG. 8F and FIG. 8J, and the lysis buffer in the reagent trough 120f and the proteinase K in the reagent trough 120i are drawn to the processing chamber 120a by the plunger 126.

Next, the rotating component 124 is rotated so that the guiding channel 124a is aligned with the section processing unit 150 (illustrated in FIG. 1) as shown in FIG. 8A, and the lysis buffer and the proteinase K in the processing chamber 120a is driven to move to the section processing unit 150 by the plunger 126. After the section processing unit 150 performs a heating reaction to separate out the target molecule, the liquid at the section processing unit 150 is firstly drawn to the processing chamber 120a by the plunger 126, and then the rotating component 124 is rotated so that the guiding channel 124a is aligned with the reagent trough 120d as shown in FIG. 8D. The capture buffer in the reagent trough 120d is drawn to the processing chamber 120a by the plunger 126. After the liquid in the processing chamber 120a is thoroughly blended, the rotating component 124 is rotated so that the guiding channel 124a is aligned with the first tube 140 as shown in FIG. 8I. The first tube 140 is temporarily connected between the purification unit 120 and the waste liquid trough 170 (or the first tube 140 is temporarily detached and another tube is connected between the purification unit 120 and the waste liquid trough 170). The solution carrying the target molecule is pushed from the processing chamber 120a to the glass fibre membrane at the intersection of the purification unit 120 and the first tube 140 by the plunger 126. The target molecule remains on the glass fibre membrane, and the waste liquid with other impurities is discharged to the waste liquid trough 170.

Then, the rotating component 124 is rotated so that the guiding channel 124a is aligned with the reagent trough 120e as shown in FIG. 8E, and the wash buffer in the reagent trough 120e is drawn to the processing chamber 120a by the plunger 126 to perform washing. The rotating component 124 is rotated so that the guiding channel 124a is aligned with the first tube 140 as shown in FIG. 8I, and the solution carrying the target molecule is pushed from the processing chamber 120a to the glass fibre membrane at the intersection of the purification unit 120 and the first tube 140 by the plunger 126. The target molecule remains on the glass fibre membrane, and the waste liquid with other impurities is discharged to the waste liquid trough 170. The rotating component 124 is rotated so that the guiding channel 124a is aligned with the reagent trough 120h as shown in FIG. 8H, and the wash buffer in the reagent trough 120h is drawn to the processing chamber 120a by the plunger 126 to perform washing. The rotating component 124 is rotated so that the guiding channel 124a is aligned with the first tube 140 as shown in FIG. 8I, and the solution carrying the target molecule is pushed from the processing chamber 120a to the glass fibre membrane at the intersection of the purification unit 120 and the first tube 140 by the plunger 126. The target molecule remains on the glass fibre membrane, and the waste liquid with other impurities is discharged to the waste liquid trough 170.

Next, the rotating component 124 is rotated so that the guiding channel 124a is aligned with the reagent trough 120g as shown in FIG. 8G, and the amplification buffer in the reagent trough 120g is drawn to the processing chamber 120a by the plunger 126. The rotating component 124 is rotated so that the guiding channel 124a is aligned with the first tube 140 as shown in FIG. 8I. The first tube 140 is connected between the purification unit 120 and the metering unit 130, and the solution carrying the target molecule is transferred from the processing chamber 120a to metering unit 130 by the plunger 126, such that the solution carrying the target molecule is blended with the amplification enzyme in the metering trough 130b of the metering unit 130. A thermal cycling process is performed to the solution in the metering trough 130b and a fluorescent signal detection is performed by the detection device 50 instantaneously.

In sum, the biological sample processing device of the disclosure integrates the purification unit and the metering unit onto the same base, such that the sample purified by the purification unit may be directly transmitted to the metering unit to be metered, and then a detection operation is performed to the sample in the metering unit. Accordingly, there is no need to manually transfer the biological sample between multiple machines as the conventional detection process does, so as to avoid cross contamination of biological sample and infection of biological waste, and save operation time and labor cost for detection. In addition, in the metering unit of the disclosure, the metering trough is designed to be connected between the inlet and the overflow trough, such that the sample would indeed fill up the metering trough before flowing to the overflow trough, so as to determine whether the sample is indeed metered in the metering trough or not according to whether the sample appears in the overflow trough or not.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A biological sample processing device, comprising:
   a base;
   a purification unit disposed on the base and configured comprising a processing chamber to purify a sample;
   a metering unit disposed on the base and aside the purification unit, the metering unit comprising an inlet, at least one metering trough, and an overflow trough disposed above the at least one metering trough, wherein the inlet is connected to the purification unit, the at least one metering trough is connected between the inlet and the overflow trough, the sample flows from the purification unit enters the metering unit through the inlet to the metering trough, and overflows toward the overflow trough; and
   a first tube, wherein the inlet of the metering unit is connected to the purification unit via the first tube.

2. The biological sample processing device as claimed in claim 1, wherein the metering unit has a first channel and a second channel, the first channel is connected between the inlet and a side of the at least one metering trough, the second channel is connected between the side of the at least one metering trough and the overflow trough.

3. The biological sample processing device as claimed in claim 1, wherein the metering unit has a first channel and a second channel, the first channel is connected between the inlet and the at least one metering trough, the second channel is connected between the at least one metering trough and the overflow trough, and an interface between the second channel and the at least one metering trough is higher than an interface between the first channel and the at least one metering trough.

4. The biological sample processing device as claimed in claim 1, wherein the at least one metering trough has a first end and a second end opposite to each other, the sample enters the at least one metering trough from the first end, a cross-sectional width of at least a part of the at least one metering trough increases from the first end to the second end.

5. The biological sample processing device as claimed in claim 1, wherein a first shortest distance between a first plane where the at least one metering trough is disposed on and a second plane where the base is disposed on is shorter than a second shortest distance between a third plane where the overflow trough is disposed on and the second plane where the base is disposed on.

6. The biological sample processing device as claimed in claim 1, wherein the metering unit has a detection surface, the detection surface is a transparent end surface and the at least one metering trough is exposed by the transparent end surface, a detection device detects the sample in the at least one metering trough via the detection surface.

7. The biological sample processing device as claimed in claim 1, wherein
the metering unit comprises a plurality of the at least one metering trough a main body, and a rotating component,
the inlet, the plurality of the at least one metering trough and the overflow trough are disposed on different sides of the main body,
the plurality of the at least one metering trough and the inlet are disposed at two opposing sides of the rotating component, and
the rotating component comprises a containing chamber and a guiding channel, and the rotating component is rotatable to allow the guiding channel to be in communication with the inlet or any one of the plurality of the at least one metering trough.

8. The biological sample processing device as claimed in claim 7, wherein the metering unit comprises a plunger, and the plunger is connected to the rotating component and moves in opposing directions to drive the sample in or out of the containing chamber.

9. The biological sample processing device as claimed in claim 8, wherein the plunger has a covering portion covering the overflow trough along with a motion of the plunger.

10. The biological sample processing device as claimed in claim 1, wherein the metering unit has at least one heating surface overlapping the at least one metering trough to heat the sample in the at least one metering trough so as to undergo an amplifying reaction.

11. The biological sample processing device as claimed in claim 1, wherein the purification unit comprises a sample trough and a plurality of reagent troughs, the processing chamber is connected to the inlet of the metering unit via the first tube, the sample trough contains the sample, the plurality of reagent troughs contains a plurality of reagents, the sample is moved to the processing chamber from the sample trough, and each of the plurality of reagents is moved to the processing chamber from one of the plurality of reagent troughs to purify the sample in the processing chamber.

12. The biological sample processing device as claimed in claim 11, wherein the purification unit comprises a main body and a rotating component, the sample trough and the plurality of reagent troughs are located inside the main body, the processing chamber is located inside the rotating component, the rotating component has a guiding channel connected to the processing chamber, and the rotating component is rotatable to allow the guiding channel to be in communication with the sample trough or any one of the plurality of reagent troughs.

13. The biological sample processing device as claimed in claim 12, wherein the purification unit comprises a plunger, the plunger is connected to the rotating component and moves in opposing direction to drive the sample and each of the plurality of reagents in or out of the processing chamber.

14. The biological sample processing device as claimed in claim 1, further comprising a section processing unit, wherein the section processing unit is disposed on the base and aside the purification unit and the metering unit, and the section processing unit is connected to the purification unit via a second tube, the section processing unit contains a sample section, and the sample is obtained from the sample section.

15. The biological sample processing device as claimed in claim 14, wherein the section processing unit comprises a body having a containing space and a gateway disposed on the body, the containing space contains the sample section and is connected to the purification unit via the gateway, the containing space has at least one guiding slanted surface guiding the sample flow toward the gateway.

16. The biological sample processing device as claimed in claim 15, wherein the section processing unit comprises a heating assembly disposed on the body and heating the sample section so as to perform a deparaffinization to the sample section.

17. The biological sample processing device as claimed in claim 1, further comprising a waste liquid trough disposed on the base aside the purification unit and the metering unit and connected to the purification unit to discharge a waste liquid generated by the purification unit.

* * * * *